United States Patent [19]

Goldberger et al.

[11] Patent Number: 5,249,576
[45] Date of Patent: Oct. 5, 1993

[54] UNIVERSAL PULSE OXIMETER PROBE

[75] Inventors: Daniel S. Goldberger, Boulder; Timothy A. Turley, Highlands Ranch; Kirk L. Weimer, Englewood, all of Colo.

[73] Assignee: BOC Health Care, Inc., Liberty Corner, N.J.

[21] Appl. No.: 781,891

[22] Filed: Oct. 24, 1991

[51] Int. Cl.$^5$ .............................................. A61B 5/00
[52] U.S. Cl. ..................................... 128/632; 128/634
[58] Field of Search ................ 128/632, 633, 634, 637

[56] References Cited

U.S. PATENT DOCUMENTS

| | | | |
|---|---|---|---|
| 4,653,498 | 3/1987 | New, Jr. et al. | 128/633 |
| 4,685,464 | 8/1987 | Goldberger et al. | 128/633 |
| 4,700,708 | 10/1987 | New, Jr. et al. | 128/633 |
| 4,824,242 | 4/1989 | Frick et al. | 128/637 |
| 4,825,872 | 5/1989 | Tan et al. | 128/633 |
| 4,825,879 | 5/1989 | Tan et al. | 128/633 |
| 4,834,532 | 5/1989 | Yount | 128/633 |
| 4,867,165 | 9/1989 | Noller et al. | 128/633 |
| 4,928,691 | 5/1990 | Nicolson et al. | 128/633 |
| 4,964,408 | 10/1990 | Hink et al. | 128/633 |
| 5,035,243 | 7/1991 | Muz | 128/633 |
| 5,054,488 | 10/1991 | Muz | 128/633 |
| 5,080,098 | 1/1992 | Willett et al. | 128/633 |
| 5,090,410 | 2/1992 | Saper et al. | 128/633 |

OTHER PUBLICATIONS

R. C. Moore, J. A. Fulton and W. R. Lambert; "Reliability of Anisotropically Conductive Elastomer Interconnections"; AT&T Bell Laboratories.

R. C. Moore, E. J. Leddy, W. R. Lambert and T. H. Tiefel; "Testing Bare Boards with an Anisotropically Conductive Elastomer"; pp. 47-56.

W. R. Lambert, J. P. Mitchell, J. A. Suchin and J. A. Fulton; "Use of Anisotropically Conductive Elastomers in High Density Separable Connectors"; pp. 99-106.

J. A. Fulton, D. R. Horton, R. C. Moore, W. R. Lambert, S. Jin, R. L. Opila, R. C. Sherwood, T. H. Tiefel and J. J. Mottine; "Electrical and Mechanical Properties of a Metal-Filled Polymer Composite for Interconnection and Testing Applications"; pp. 1-7.

AT&T; "Elastomeric Conductive Polymer Interconnect"; Jul. 1989.

Fujipoly; "Connector W Series".

Stan Gage, Dave Evans, Mark Hodapp, Hans Sorensen, Dick Jamison and Bob Krause; "Optoelectronics/Fiber-Optics Applications Manual"; pp. 15.1-15.23.

*Primary Examiner*—Randall L. Green
*Assistant Examiner*—G. Gualtheri
*Attorney, Agent, or Firm*—Roger M. Rathbun; Larry R. Cassett; R. Hain Swope

[57] ABSTRACT

The universal pulse oximeter probe [of the present invention] utilizes an inexpensive sensor connector configuration to enable the cable section of the probe to be used numerous times. The [sensor connector is mechanically simple and electrically reliable to interconnect the sensor elements with the cable that connects the pulse oximeter system to the sensor elements. This sensor connector enables the user to obtain significant benefits due to the fact that the expensive cable segment of the probe is a separable element from the housing that contains the sensor elements. In particular, the] cable segment of the probe consists of a connector that is compatible with the pulse oximeter system and which functions to interconnect the pulse oximeter system with a plurality of conductors, the far end of which are terminated in the sensor connector [of the present invention]. The probe housing contains a mating element to this sensor connector, the sensor elements and a means of mechanically affixing the sensor elements to the subject. Thus, the cable end of the probe is reusable numerous times and the disposable part of the probe only consists of the housing with the sensors. Furthermore, the housing containing the sensors is electrically configured to be generic to all pulse oximeter system. In this regard, the active elements and passive elements contained therein are directly connected to the sensor connector without interconnection amongst themselves. Jumper leads are provided within the cable half of the sensor connector to electrically interconnect these elements in a manner that is appropriate for the associated pulse oximeter system.

49 Claims, 9 Drawing Sheets

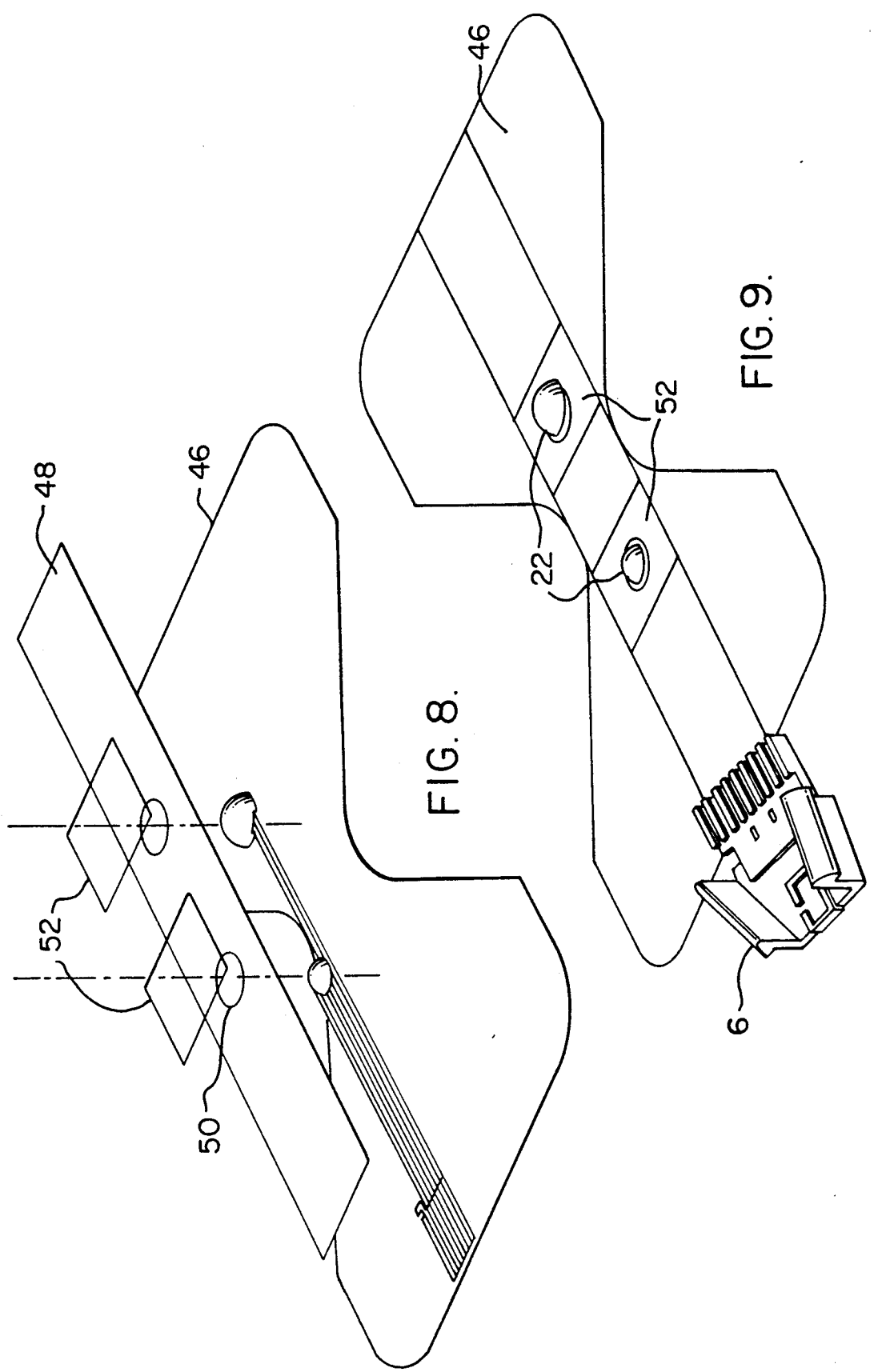

UNIVERSAL PULSE OXIMETER PROBE

FIELD OF THE INVENTION

This invention relates to medical monitoring equipment and, in particular, to an inexpensive disposable universal probe, containing sensor elements, that interfaces to a plurality of different pulse oximeter instruments.

PROBLEM

It is a problem in the field of monitoring equipment in biomedical technology to produce a probe, including sensor elements, that is inexpensive, simple to use, accurate in their measurements and yet disposable. In the field of pulse oximetry, the pulse oximeter instrument is connected to a subject via a disposable probe, which is connectorized to be detachable from the pulse oximeter instrument. The probe includes a sensor circuit that consists of a pair of light emitting diodes and a photodetector that are incorporated into a housing that can be applied to the subject in order to measure the oxygenation of the subject's blood. Present pulse oximeter probes use a connectorized long cable, hard-wired at one end to the light emitting diodes and light detector. The housing can be of many configurations due to the fact that the pulse oximeter instrument is used with adult subjects, children and infants. Each of these classes of subjects may require a different means of attaching the active sensor elements to a blood carrying member of the subject. For example, the sensors can be attached to the subject's finger, ear, foot or septum, each of which application requires a different housing for the sensors. Another complicating factor is that each pulse oximeter instrument utilizes a different connector configuration and possibly a different sensor element wiring configuration in the probe.

It is obvious that a hospital must stock a large diversity of pulse oximeter probes, each of which is a disposable element. The proliferation of probe types produces an inventory problem as well as increased cost to the patient, since a significant segment of the manufacturing costs of the probe is the connector and associated wiring that interconnects the sensor elements to the pulse oximeter instrument. The manufacturers of pulse oximeter probes also do not have the economies of scale of making a single probe but instead must manufacture numerous different incompatible probes.

SOLUTION

The above described problems are solved and a technical advance achieved in the field by the universal pulse oximeter probe of the present invention which utilizes an inexpensive sensor connector configuration to enable the probe connector/cable section of the probe to be used numerous times. The sensor connector is both mechanically simple and electrically reliable and functions to interconnect the housing containing the sensor elements with the cable that connects the pulse oximeter instrument to the sensor elements. This sensor connector enables the user to obtain significant benefits due to the fact that the expensive cable segment of the probe is a separable element from the housing segment of the probe that contains the sensor elements.

In particular, the cable segment of the probe consists of a probe connector that is compatible with the pulse oximeter instrument and which functions to interconnect the pulse oximeter instrument with a plurality of conductors, the far end of which are terminated in one half of the sensor connector of the present invention. The probe housing contains the mating other half of this sensor connector, the sensor elements and a means of mechanically affixing the sensor elements to the subject. Thus, the cable segment of the probe is reusable numerous times and the disposable part of the probe consists only of the housing with the sensor elements. This significantly reduces the cost of pulse oximeter probes since the most significant cost element in the probe, the cable and probe connector, can be amortized over numerous uses. Furthermore, the housing containing the sensors is electrically configured to be generic to all pulse oximeter instruments. In this regard, the active elements and passive elements contained therein are directly connected to the sensor connector without interconnection amongst themselves. Jumper leads are provided within the cable segment of the probe to electrically interconnect these elements in a manner that is appropriate for the associated pulse oximeter instrument. Therefore, only a limited number of types of cable segments need be used to interconnect the various models of pulse oximeter instruments to the sensors contained within the housing. The housing variability is solely a function of the needs of the particular subject and unrelated to connector and sensor element wiring variations in pulse oximeter instruments. The pulse oximeter instrument variability is accounted for in the cable segment of the probe, since it provides the probe connector that is specific to the pulse oximeter instrument and the associated sensor element interconnection wiring that is also specific to the pulse oximeter instrument. Therefore, the cost of manufacturing the housing elements is significantly reduced since they are more of a commodity item, useable for all pulse oximeter instruments. The economic viability of this configuration is largely due to the inexpensive connector that is used thereon.

The sensor connector must satisfy a number of fairly stringent requirements in order to be useable in this application. In particular, the sensor connector must be mechanically rugged in order to withstand numerous uses in a relatively unprotected environment. Furthermore, the sensor connector must be mechanically simple and yet contain a latching mechanism to prevent accidental disconnection of the two sensor connector halves. The electrical contacts contained in the sensor connector must also be simple in construction in order to minimize the cost and yet provide a low resistance, electrically continuous interconnection of the sensor elements to the pulse oximeter instrument. Any noise that is introduced into the signals produced by the probe's sensor elements significantly impairs the functioning of the pulse oximeter system. The conductors in both halves of the sensor connector must therefore be precisely aligned with each other in order to provide good electrical contact therebetween when the sensor connector halves are latched together.

In order to satisfy these diverse requirements, a flat lead frame is used in the housing to electrically interconnect the sensor elements with a first half of the sensor connector. The flat conductors of the lead frame mate with corresponding flat conductors in the second sensor connector half in the cable segment of the probe. The mechanical configuration of this sensor connector is such that a spring clip is used to latch the two halves of the sensor connector together. The mechanical orientation is accomplished by the use of geometrically matching elements in the two connector halves. In order to provide the electrical conductivity necessary, a layer of anisotropically conducting elastomer is applied over the conductors of the cable half of the sensor connector. This elastomer consists of a plurality of metallic spheres embedded in a nonconductive polymer material. During manufacture of the elastomer, a magnetic field is applied to an admixture of the conductive spheres and polymer material in order to align the metallic spheres in a preferred direction along the thickness of this material. The elastomer is then cured to retain the conductive spheres in the orientation created by the magnetic field. The resultant elastomer material consists of a nonconductive polymer through which are provided a plurality of conductive paths from one surface to the other across the thickness dimension of the elastomer. Thus, any physical misalignment of the conductors of the two sensor connector halves due to motion within the sensor connector during its use does not cause loss of conductivity, since the elastomer flexes in a transverse direction without interrupting the conductivity of the columns of conductive spheres. This minimizes the need for precision alignment of the two sensor connector halves, thereby reducing the cost of manufacture of the sensor connector. In addition, the elastomer covers the conductors and renders them impervious to moisture.

Therefore, the use of this inexpensive yet efficient sensor connector arrangement enables the creation of universal housing configurations which are physically and electrically customized to the pulse oximeter instrument of choice by means of a cable segment of the probe which provides a probe connector specific to the desired pulse oximeter instrument as well as the electrical interconnection of the sensor elements necessary for the universal housing to be compatible with the particular pulse oximeter instrument.

BRIEF DESCRIPTION OF THE DRAWING

FIGS. 8 and 9 illustrate details of the lead frame and housing construction;

DETAILED DESCRIPTION

Figure 1:
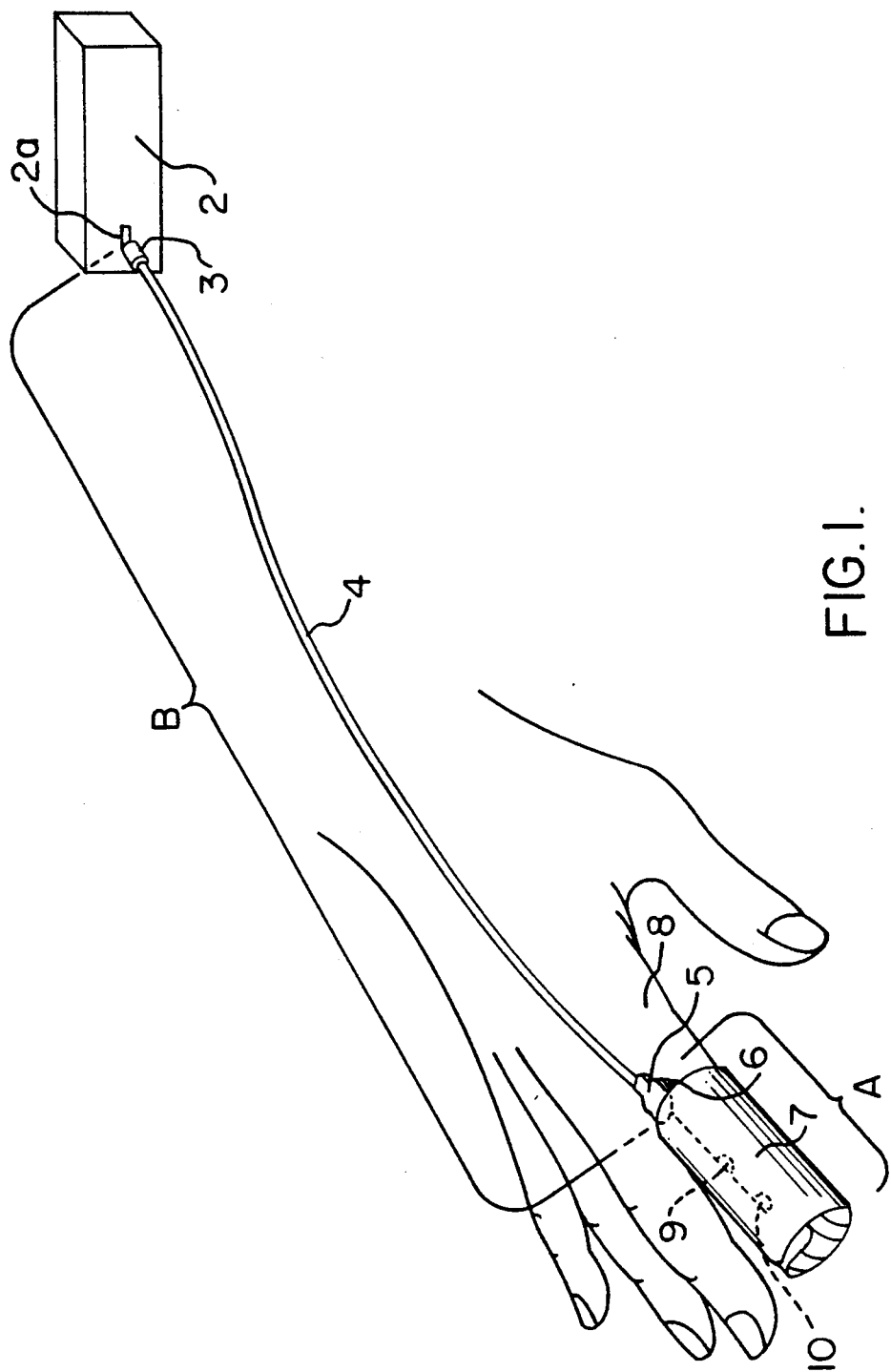
FIG. 1 illustrates, in block diagram form, the overall architecture of the pulse oximeter probe of the present invention.

FIG. 1 illustrates in block diagram form the overall system architecture of the universal pulse oximeter probe 1 of the present invention. A pulse oximeter instrument 2 is a well known device used extensively in critical care areas or hospitals to monitor a subject's arterial percentage oxygen saturation ($SpO_2$) and pulse rate (PR). The pulse oximeter instrument 2 performs these measurements by recording the absorption of light in perfused tissue at two or more wavelengths of light. The pulse oximeter instrument 2 compares the time variant and time invariant portions of the light absorption signal at the two wavelengths of light and uses this data in a well known empirical relationship to compute both the pulse rate and arterial percentage oxygen saturation.

In order to perform the measurements on the subject, the pulse oximeter system includes a probe 1 which is releasably attached to the subject 8. In a typical application, the probe 1 is releasably affixed to a subject's finger 8 or other arterial rich member of the body. The methods of releasably attaching the probe to the subject are well known in this technology and consist of mechanical clips, adhesively backed webs, and velcro webs of numerous configurations and dimensions. The probe 1 therefore includes at the distal end thereof a housing 7 that carries the sensor elements 9, 10 and the means of releasably attaching the probe to the subject.

A typical configuration of sensor elements 9, 10 includes first and second light sources 9, each of which generates a beam of light centered about a predefined wavelength. The wavelengths of these two light sources differ and are selected to detect the desired characteristics of the arterial blood as is well known in the art. The two light sources 9 are placed in the housing 7 in a manner to project the beams of light generated into the arterial tissue 8 in order to illuminate this tissue. The housing furthermore includes a light detector 10 which is positioned to measure the amount of light transmitted through the arterial tissue 8 of the subject. Typically, the two light sources 9 are activated in sequence in order that a single wavelength of light illuminates the arterial bed at a time in order to enable the single light detector 10 to measure the absorption of that wavelength of light by the arterial tissue 8. The light sources 9 are driven by pulse signals produced by the pulse oximeter instrument 2 and applied thereto via a probe connector 3 which serves to mechanically and electrically interconnect the probe 1 with a corresponding connector 2a on the pulse oximeter instrument 2. A cable 4 containing a plurality of conductors is used to hard wire the light sources 9 and light detector 10 to the probe connector 3 which plugs into a corresponding connector 2a on the pulse oximeter instrument 2. The various pulse oximeter instruments 2 electrically interconnect the light sources 9, and light detector 10 in a variety of ways in order to perform the required measurements. In the prior art, each probe 1 is manufactured to be specific to a single model of pulse oximeter instrument 2 and also must be manufactured to be application specific as a function of the body part 8 to which it is attached and the nature of the subject: adult, child, infant. Therefore, the variability of subject is complicated further by the additional variable of pulse oximeter specific wiring required. These factors all contribute to the cost of the pulse oximeter probes since the probes are disposable and the greater the number of models required, the greater the cost to manufacture since there is a reduction in commonality of usage. Furthermore, the cable 4 and connector 3 end of the probe represents a significant manufacturing cost that is absorbed by the subject in the single use of the probe 1.

Universal Pulse Oximeter Probe Architecture

In order to reduce the cost of probes in pulse oximeter systems, the universal probe 1 of the present invention makes use of an inexpensive sensor connector 5, 6 to separate the truly disposable housing 7 and sensor element segment A of the probe 1 from the expensive and reusable cable/connector segment B of the probe 1. By dividing the probe into two sections A, B, the cost of the cable/connector segment B of the probe 1 can be amortized over numerous uses, thereby reducing the cost to the subject. Furthermore, the pulse oximeter instrument specific wiring an be implemented in the reusable portion B of the probe 1, to enable the housing segment A of the probe 1 to be of a universal configuration applicable to all pulse oximeter instruments 2 and having only a single degree of freedom: the application to a specific body part or subject class.

Figure 2:
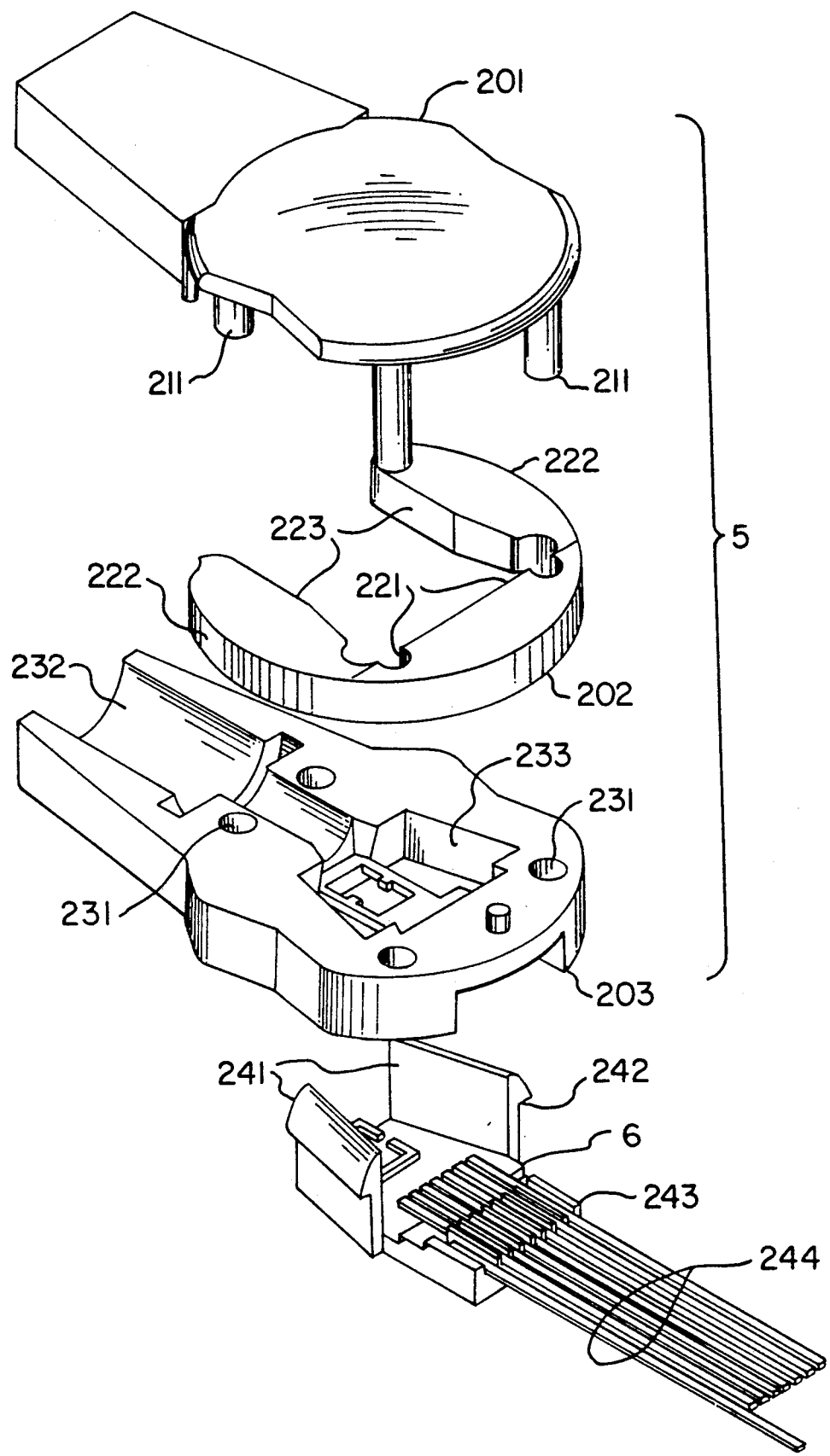
FIG. 2 illustrates an exploded view of the sensor connector.
Figure 3:
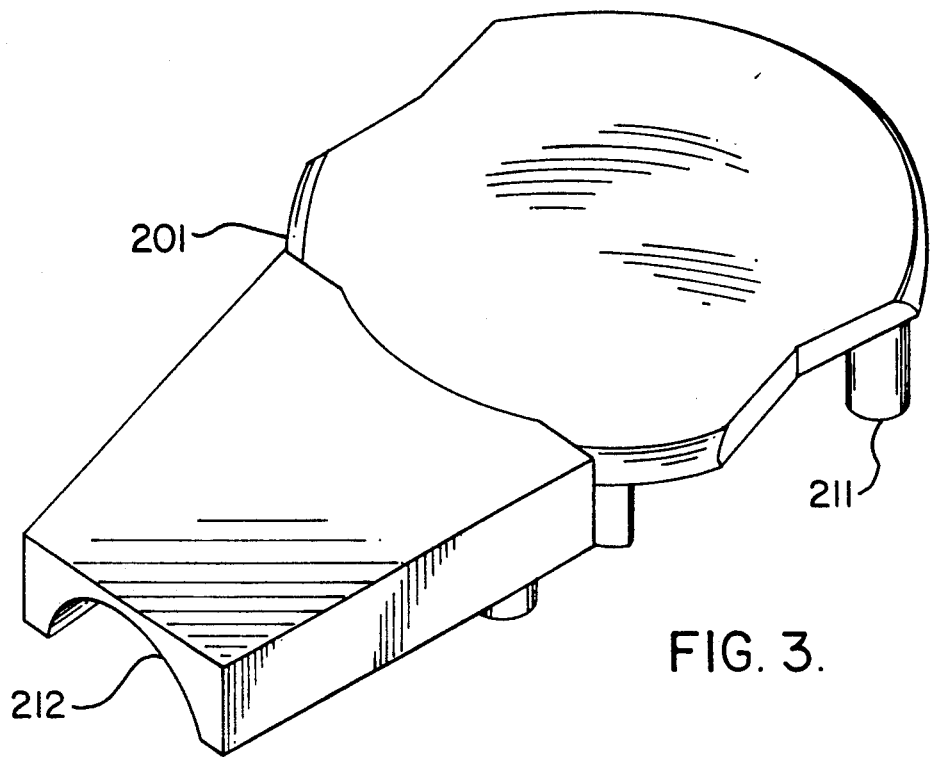
FIGS. 3 and 4 illustrate isometric views of the top and bottom of the cap of the cable half of the sensor connector, respectively.
Figure 4:
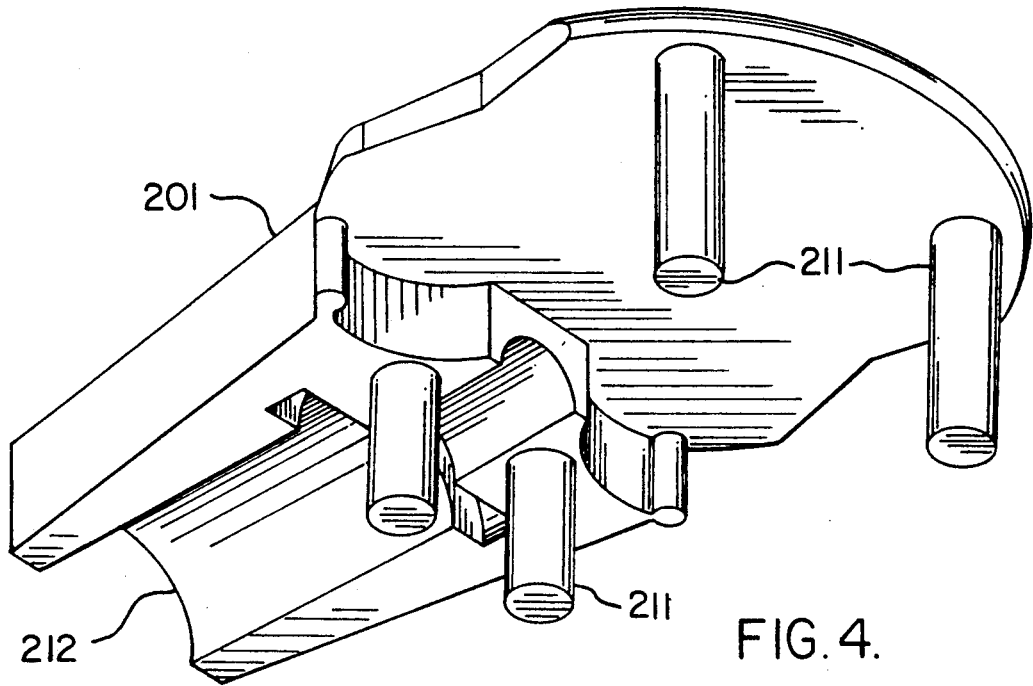
Figure 5:
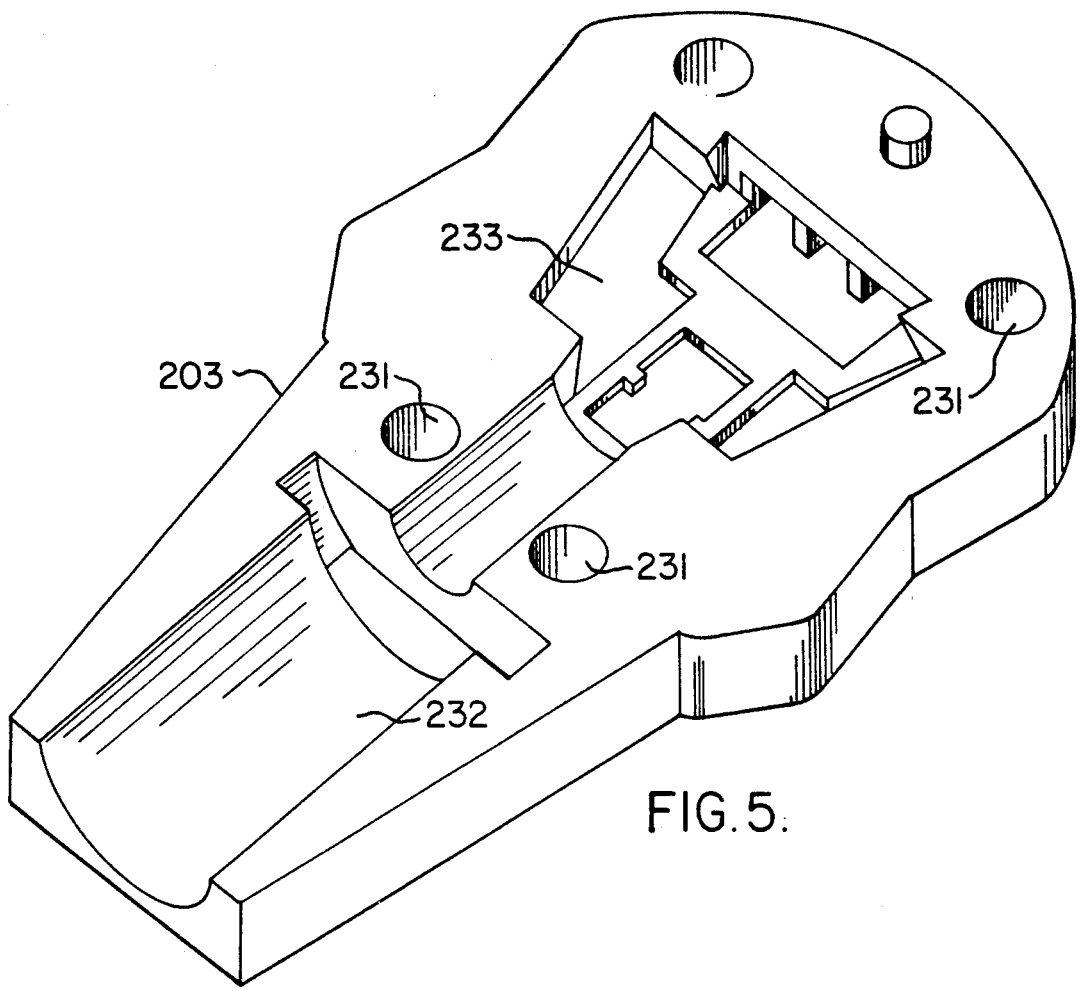
FIGS. 5 and 6 illustrate isometric views of the top and bottom of the base of the cable half of the sensor connector, respectively.
Figure 7:
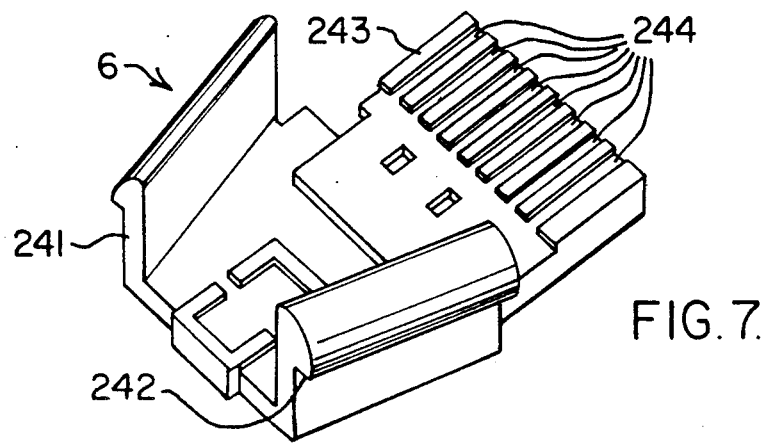
FIG. 7 illustrates additional details of the housing half of the sensor connector.
Figure 6:
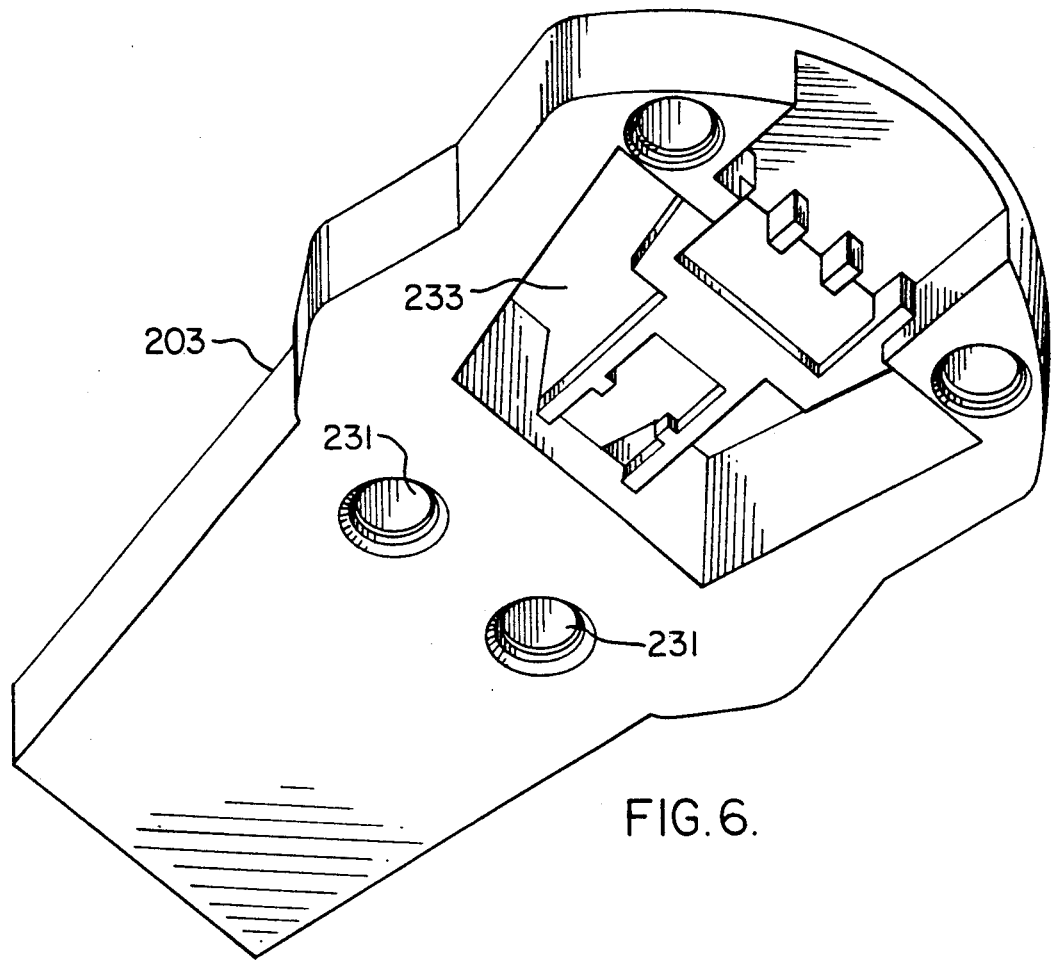

The universal pulse oximeter probe 1 is illustrated in block diagram form in FIG. 1 and FIG. 2 illustrates an exploded view of the sensor connector 5, 6 that is used to segment the universal pulse oximeter probe 1 into two segments A, B. In the illustration of FIG. 1, the pulse oximeter instrument 2 is connected via a probe connector 3 to a cable 4 in conventional fashion in order to electrically and mechanically interconnect the probe 1 to the circuitry of the pulse oximeter instrument 2. One end of the cable 4 is connected to a sensor connector 5, 6 which consists of a plurality of elements illustrated in exploded view in FIG. 2. The cable half 5 of the sensor connector 5, 6 consists of a base 203, a cap 201, and a spring clip 202 interposed therebetween. The base 203 includes a plurality of holes 231 into which corresponding pins 211 on the cap 201 seat to interlock and position the various pieces of the connector 5. The spring clip 202 is horseshoe shaped and includes a plurality of notches 221 therein which notches 221 mate with the pins 211 of the cap 201 in order to position the spring clip 202 in the proper orientation in the cable half 5 of the sensor connector 5, 6. To mechanically assemble the cable half 5 of the sensor connector 5, 6 the spring clip 202 is positioned on the base 203 and the cap 201 placed on top of the spring clip 202 such that the pins 211 of the cap 201 fit through the notches 221 in the spring clip 202 and the holes 231 in the base 203. The pins 211 are then staked or ultrasonically welded in place in order to form a unitary locked structure.

The spring clip 202 is deformable such that, in the extended position, the edges 222 of the spring clip 202 extend beyond the periphery of the cap 201 and the base 203. When the spring clip 202 is compressed by a user applying force to the clip edges 222, the edges 222 are recessed such that they are flush with the periphery of the cap 201 and the base 203.

Both the cap 201 and the base 203 include a channel 212, 232 that receives the cable 4 as well as a support 12 (FIG. 14) that positions the conductors of the cable 4 in a spaced apart relationship such that they are parallel to each other, a predetermined distance apart, and electrically insulated from each other. The conductors 244 in the housing end 6 of the sensor connector 5, 6 are similarly supported and spaced apart in order to enable the mechanical alignment of the conductors 244 to provide electrical continuity between the two halves of sensor connector 5, 6 when interconnected. The housing segment 6 of the sensor connector 5, 6 consists of a U-shaped molded plastic piece with the two vertical arms 241 thereof having a lip 242 thereon for engagement of the cable half 5 of the sensor connector 5, 6. Thus, when the two halves of the sensor connector 5, 6 are placed together, the U-shaped arms 241 of the housing half 6 of the sensor connector 5, 6 pass through a corresponding opening 233 in the base 203 of the cable half 5 of the sensor connector 5, 6 and are deformed inwardly toward each other by the force applied by the user to join the two sensor connector halves 5, 6. The plastic is springably deformable such that the two arms 241 of the housing connector 6 flex inwardly until they pass through the base 203 of the cable half 5 of the sensor connector 5, 6 whereupon they expand outward with the lip 242 of the arms 241 resting on the top side of the base 203 of the cable half 5 of the sensor connector 5, 6 to form a mechanically secure joining of the two sensor connector halves 5, 6. The spring clip 202 in the cable half 5 of the sensor connector 5, 6 is deformable inwardly by the user applying pressure to the two edges 222 thereof that extend beyond the periphery of the cap 201 and the base 203 of the cable half 5 of the sensor connector 5, 6. The deformation of the spring clip 202 causes the inside edges 223 of the spring clip to engage the arms 241 of the housing half 6 of the sensor connector 5, 6, causing deformation thereof such that the lip 242 of the arms 241 of the housing half 6 of the sensor connector 5, 6 are pressed inward to clear the inner edge of the opening 233 in the base 203 of the cable half 5 of the sensor connector 5, 6, enabling the user to separate the two halves of the sensor connector 5, 6. This sensor connector 5, 6 is a simple configuration that requires little manufacturing and yet provides a fairly secure mechanical interconnection of the cable B and housing A segments of the probe 1.

Housing Sensor Wiring

Figure 12:
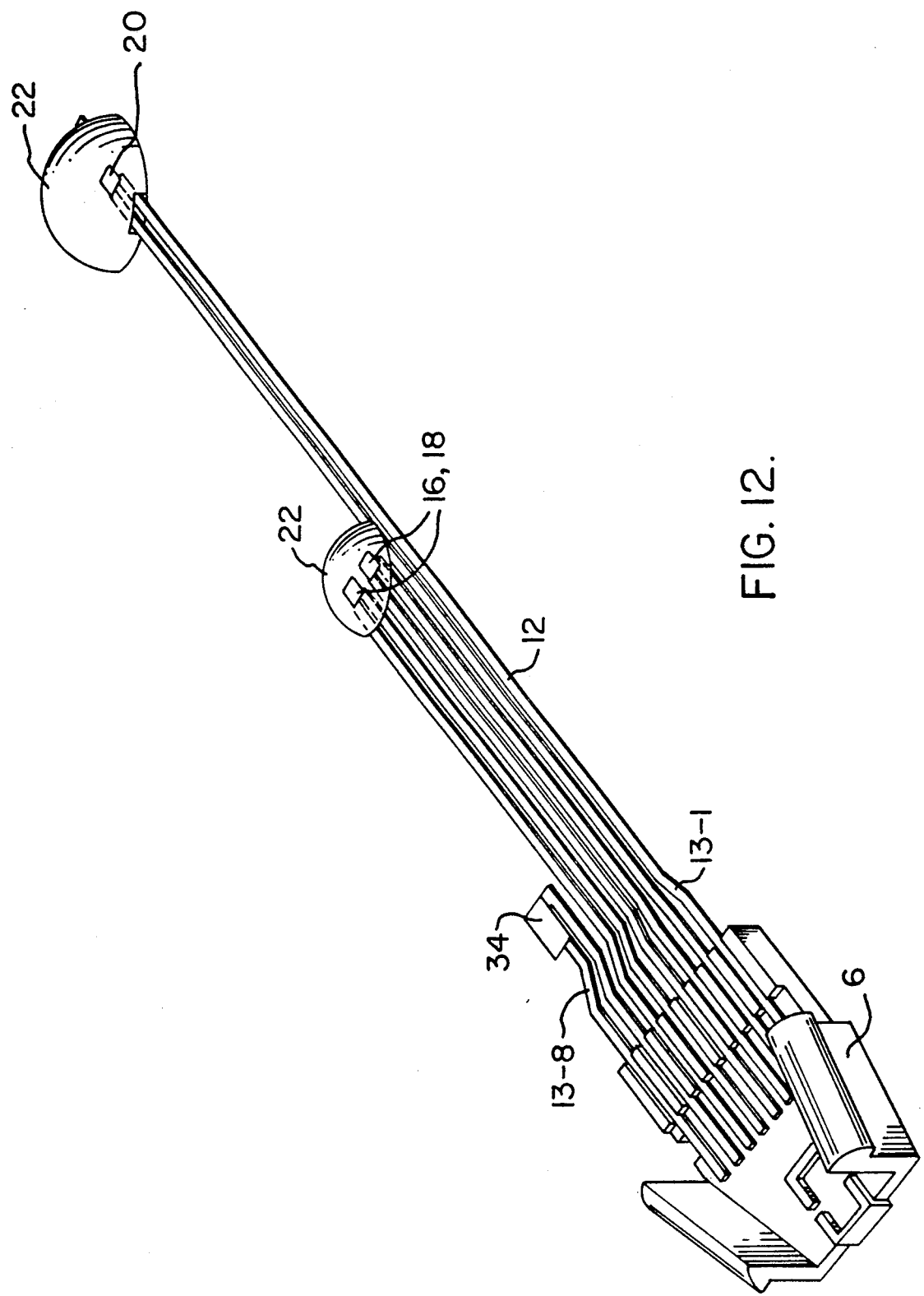
FIG. 12 illustrates additional details of the lead frame and connector configuration.

FIG. 12 illustrates the electrical and mechanical interconnection of sensor elements 16, 18, 20, 34 in the housing 7. An integrated lead frame 12 is used to provide electrical interconnection, mechanical orientation of components, and a means for attachment of sensors 16, 18, 20 to perfused tissue. In a preferred embodiment, the lead frame 12 is made from 0.1 mm to 0.3 mm thick steel or copper sheet and eight leads 13-1 to 13-8 are formed in the lead frame 12 by stamping or chemical machining. A plastic sensor connector half 6 is placed near one end of the lead frame 12 and is formed by insert molding, or attached to lead frame 12 by heat staking, ultrasonic welding or adhesive bonding. Red and infrared light emitting diodes 16, 18 ("LEDs"), a photodiode 20 and any other elements 34 (if any) are attached directly to the leads of lead frame 12. In a preferred embodiment, the attachment is made with silver filled epoxy and electrical connectors are made with gold ball or wedge bonding. Light emitting diodes 16, 18 and photodiode 20 are subsequently encapsulated in plastic lenses 22 by transfer molding or casting. The assembly is subsequently sealed in an envelope of thin, transparent plastic film (not shown) to provide electrical insulation. The insulating film may or may not be coated with pressure sensitive adhesive and it may or may not be have opaque sections between transparent windows. The electrical connector formed by the lead frame 12 and connector half 6 mates with a connector half 5 on the cable segment B of the probe 1. The device to which the pulse oximetry sensor 1 of the present invention is connected is a pulse oximeter instrument 2, such as those manufactured by Ohmeda (a division of the BOC Healthcare Group, Inc.) of Louisville, Colo. under the designation 3740.

In one preferred embodiment, the lead frame 12 is fabricated from 0.005 thick copper alloy C194 with 0.00005 inch thick nickel plating overall and with 0.000075 inch thick selective gold plating on wire bonding pads only. The lead frame 12 may also be plated with gold, silver or palladium. A suitable red light emitting diode 16 is that sold by Showa Denko of San Mateo, Calif. as part number ARH-35. This LED has a typical light output of 9 candellas at a wavelength of 655 nanometers. A suitable infrared light emitting diode 18 is that manufactured by Showa Denko of San Mateo, Calif. under part number IR-35, which has a typical light output of 0.9 milliwatts at a wavelength of 940 nanometers. silicon photodiode 20 can be obtained from Silicon Detector Corporation of Camarillo, Calif., which sells the photodiode as part number 150-3842. This photodiode 20 has a typical response of 0.5 amp/watt and a wavelength of 900 nanometers. The photodiode has an active area of 0.56 inches×0.56 inches.

The lead frame 12 provides means for electrical connection and mechanical orientation of the light sources 16, 18 and the photodetector 20 and eliminates the need for additional substrate components. The metal lead frame 12 can be formed, plated or polished as appropriate to optimize light emission or detection. The lead frame 12 also provides a mechanism for holding the photoactive components while a precision lens 22 is molded to encapsulate them. The design of such precision lenses is well known in the art as described in *Optoelectronics/Fiber-Optics Applications Manual* which is prepared by the application engineering staff of Hewlett-Packard Optoelectronics Division and is published by McGraw-Hill Book Company and the teachings of which are incorporated herein by reference. In a preferred embodiment, the precision lens 22 is molded out of a transparent, electrically insulating epoxy manufactured by Ablestick Laboratories of Gardena, Calif. under the designation Ablebond ® 342-3, which enables the lens 22 to increase the amount of light coupled into and out of the perfused tissue. The lens 22 may also be tinted to provide additional shielding from ambient light.

The lead frame 12 deforms plastically as it is bent to conform to the subject's tissue, such as a finger tip 8, so that it accurately retains its shape after it is applied to the finger tip 8. The material and thickness of the lead frame 12 can be chosen to optimize this behavior. The probe 1 can be further retained in place on the finger tip 8 by pressure sensitive adhesives or bandages so that it does not tend to spring open. The low mass and thin construction of the integrated lead frame 12 act to diminish the sensor's (16, 18, 20) susceptibility to motion induced artifact, thereby enabling the lead frame 12 to be used with a wide variety of probe designs.

The integrated lead frame probe 1 described above for use in conjunction with pulse oximeter instruments 2 lends itself to manufacture by conventional semiconductor packaging techniques. As such, the integrated lead frame probe 1 can be fabricated by highly automated equipment at low cost. The manufacturing cost is further reduced by eliminating intermediate substrates and interconnections. The lead frames 12 are generally manufactured as a panel of lead frames 12 which must then be separated. The lead frames 12 can then be supplied as a single unit or in a panel of many elements. When a panel is supplied subsequent process steps can be performed on several parts simultaneously, thereby reducing the costs of the finished probe. In addition, the external frame of the panel can include features which permit automatic parts handling for additional efficiency.

After the lead frame 12 is assembled, it is mounted in a particular type of probe 1 which can take on a variety of shapes for use with body parts such as hands, feet, fingers, toes, ears, etc. Referring to FIGS. 8 and 9, a butterfly sensor is shown which is designed for use around the tip of a finger or toe. In this embodiment, an opaque piece of tape 46 is cut into a butterfly shape. A second opaque piece of tape 48, with two openings 50 cut out to allow for the lenses 22 to pass through the openings 50, is then placed over the top surface of the lead frame 12. A transparent tape layer 52 is then placed over the top of each of the lenses 22 that protrude through the opaque tape 48.

Sensor Interconnection

Figure 10:
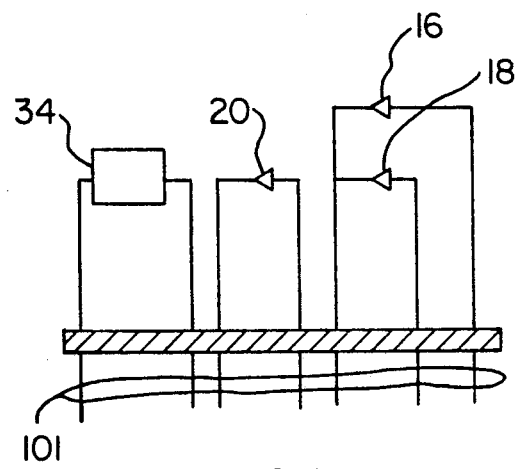
FIGS. 10 and 11 are circuit diagrams illustrative of two of the circuit interconnections used in pulse oximeter probes.
Figure 11:
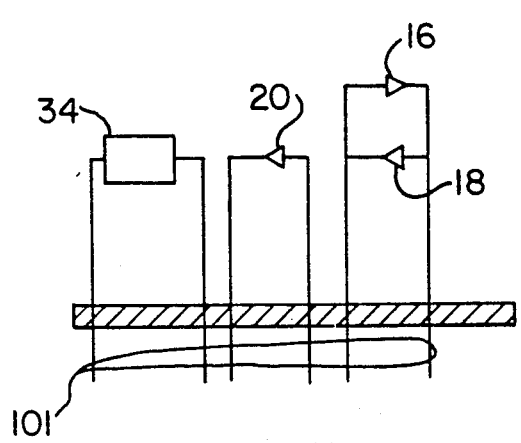

The sensors shown in FIGS. 1-9 can include various number of conductors. In the embodiment shown in FIG. 13, eight leads are shown, while other embodiments include only six or seven leads. Referring to FIG. 10, a schematic diagram for a seven lead version is shown in which two leads 100 are connected to the other elements 34, two leads 100 are connected to the photodiode 20 and the other three leads 100 are connected to the two LEDs 16, 18. In the six lead 100 embodiment shown in FIG. 11, two leads 100 are also connected to the other elements 34 and another two leads 100 are connected to the photodiode 20. The difference in the FIG. 11 embodiment is that only two leads 100 are connected to the two LEDs 16, 18. The selection of the particular lead configuration depends on the pulse oximeter system 2 that is being used with the probe 1.

A significant concern in the sensor connector system described above is the mechanical stability and electrically conductivity of the sensor connector 5, 6. In order to provide mechanical stability, the pin and socket form of connector design is used in order to precisely align the two halves of the sensor connector 5, 6. The pin 6 and socket 5 mechanical configuration are a matter of design choice and the opening 233 in the base 203 of the cable half 5 of the sensor connector is a key stone shape to receive a corresponding shaped pin from the housing half 6 of the sensor connector. It is obvious that other geometric orientations of the elements are possible and the shapes in the preferred embodiment are simply illustrative o the concept of the invention.

Anisotropically Conductive Elastomer Material

Figure 14:
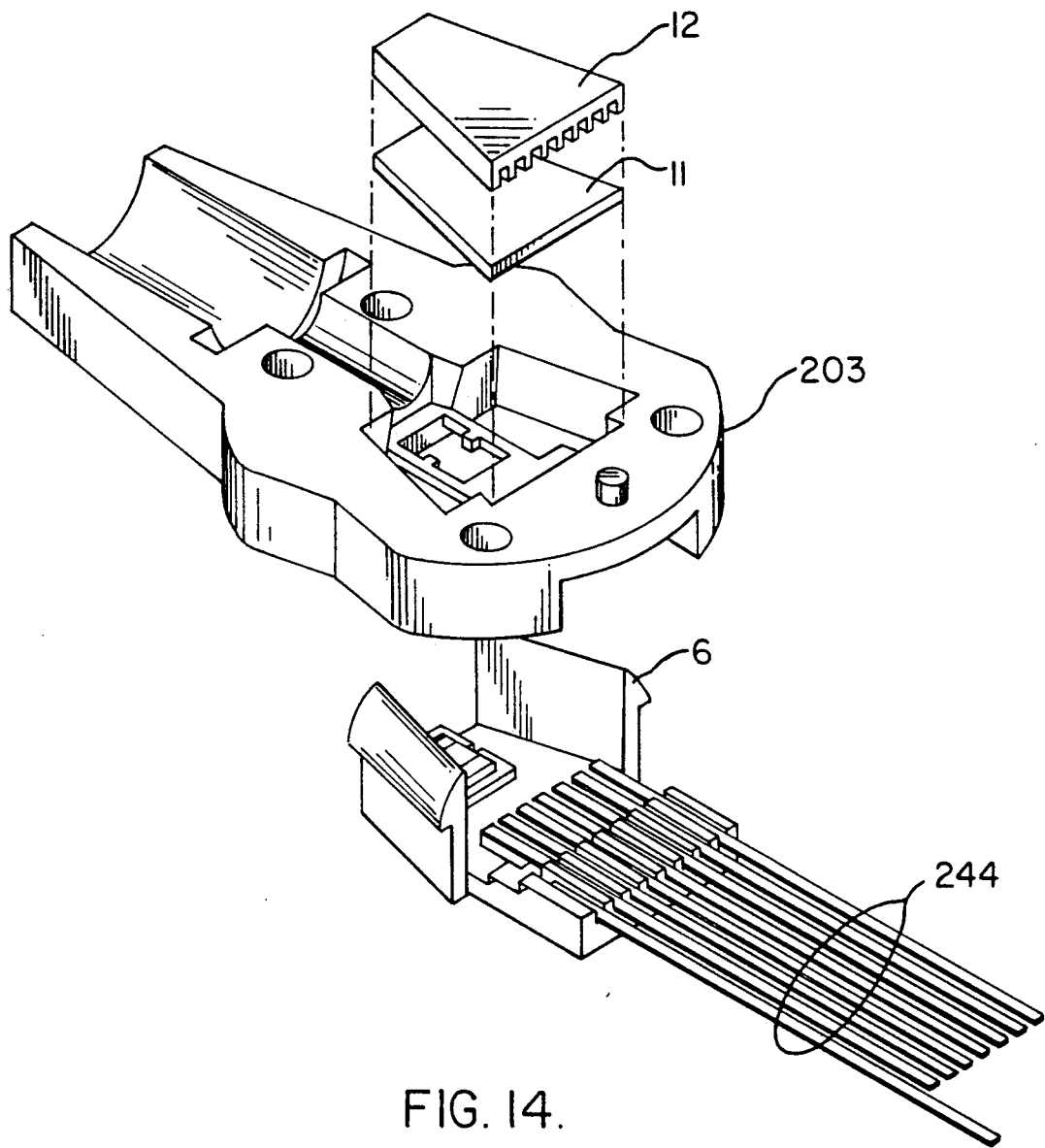
FIG. 14 illustrates an isometric view of additional details of the cable half of the sensor connector.

In order to provide electrical conductivity between the conductors of the two halves of the sensor connector 5, 6, it is important that good physical contact be made between these corresponding conductors. With the simple mechanical configuration illustrated herein, sufficient contact force between the sensor connector halves 5, 6 may not be reliably obtained. Therefore, as shown in FIG. 14, a supplementary element il is provided in order to ensure good electrical connectivity between the two sensor connector halves 5, 6 in spite of possible mechanical deformations or misalignments between the two halves of the sensor connector 5, 6. In particular, an element 11 is included in the base 203 of the cable half 5 of the sensor connector on top of the conductors attached to the support 12 contained therein. The rectangular element 11 consists of anisotropically conducting elastomer which provides electrical conductivity only in the thickness dimension thereof.

This conductive elastomer 11 is of the material group referred to as elastomeric conductive polymer interconnection (ECPI) materials. ECPIs make electrical connection between opposing contact areas using conductive columns which are regularly distributed within a sheet of silicon rubber and are separated by a spacing of seven mils or less. These materials are suitable for interconnecting high density, fine pitch pad grid arrays and are capable of accommodating tolerance variations resulting from plating thicknesses, conductor misalignment and nonplanarities between opposing contact areas. The ECPI materials can be deformed up to 40% of their uncompressed thickness without compromising their electrical properties. These ECPI materials are commercially available through AT&T Bell Laboratories, Whippany Road, Whippany, N.J. 80540. The ECPI elastomer material provides a number of advantages for this particular sensor connector. The elastomer 11 only requires light pressure to guarantee interconnection between the two surfaces thereof and provides a mechanical cushioning against shock. The elastomer material can also withstand a significant amount of transverse deformation without impacting on the conductivity thereof. Therefore, the elastomer 11 insures good electrical interconnection between the conductors of the two connector halves 5, 6 without requiring a significant contact pressure thereon. The elastomer 11 also provides electrical isolation between adjacent conductors in the two connector halves 5, 6. Furthermore, any mechanical misalignment of the sensor connector halves 5, 6 and corresponding conductors is automatically compensated for by the use of the elastomer material.

Figure 13:
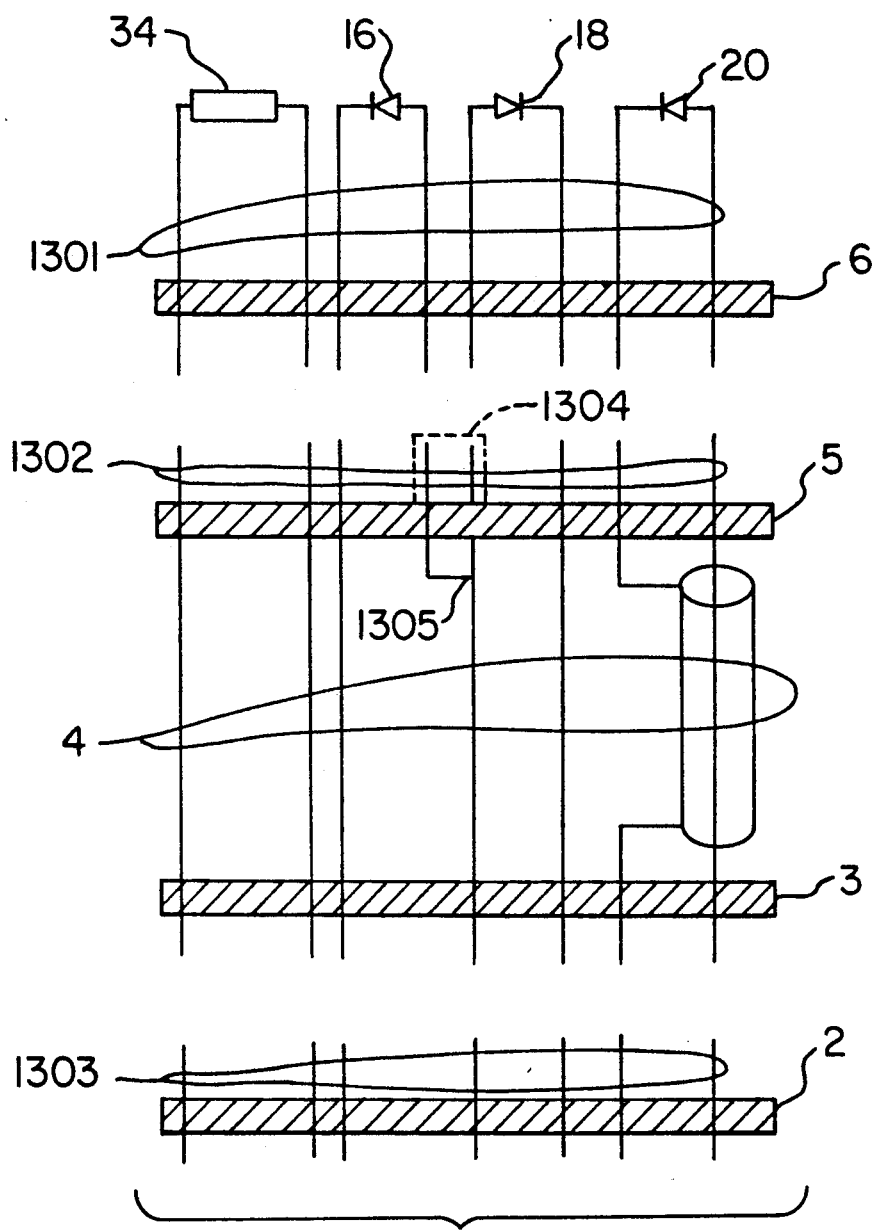
FIG. 13 illustrates a schematic diagram of the electrical interconnection of the conductors of the housing.

As was noted above, the electrical configuration the sensor 16, 18, 20 and other elements 34 within the housing 7 is a function of the pulse oximeter instrument 2 to which the probe 1 is connected. In order to provide a generic housing segment 7 of the probe 1, the leads 100 of the various devices 16, 18, 20, 34 contained therein are directly connected to corresponding conductors in the housing half 6 of the sensor connector without interconnection therebetween as shown in FIG. 13. Thus, two leads of lead frame 12 interconnect the light detector 20 while four leads interconnect the pair of light sources 16, 18 as illustrated in FIG. 13. Furthermore, the final two leads of lead frame 12 interconnect the optional other elements 34 such that the resultant circuit configuration is that illustrated in FIG. 12. The eight leads therefore provide electrical access to each terminal of every device contained within the housing 7. The resultant housing 7 is therefore generic to all pulse oximeter instruments 2 since there is no electrical interconnection of the elements 16, 18, 20, 34 contained therein and the cable segment B of the probe is used to provide the electrical interconnection to satisfy the requirements of the corresponding pulse oximeter instrument 2. The cable segment B of the probe 1 therefore physically and electrically interconnects the conductors of the cable 4 to the pulse oximeter instrument 2 as well as electrically interconnects the various conductors from the housing 7 to wire the sensor 16, 18, 20 and other 34 elements contained therein to electrically mate with the corresponding pulse oximeter instrument 2. This circuit interconnection can be accomplished in numerous way, for example, a first plurality of conductors 1301 appears in the housing half 6 of sensor connector. The cable half 5 of the sensor connector can contain a like plurality of conductors 1302 or can contain a second plurality of conductors which are less in number than the first plurality of conductors 1301. In this configuration, at least one of the conductors 1304 in the cable half 5 of the sensor connector can be of larger width than the other conductors or can be of a shape to bridge two of the conductors 1301 found in the housing half 6 of the sensor connector. In this manner, the sensor connector 5, 6 itself performs the circuit interconnection function by bridging two of the conductors from the housing 7 together. Alternatively, the support 12 contained within the cable half 5 of the sensor connector can consist of the electrical interconnection element 1305. Thus, the first plurality of conductors 1301 found in the housing half 6 of the sensor connector and the second plurality of conductors 1302 found in the cable half 5 of the sensor connector are of a like number of conductors such that each conductor in a first half of sensor connector 5, 6 has a one to one correspondence to a conductor in the second half of the sensor connector 5, 6. The pulse oximeter instrument 2 requires a third plurality of conductors 1303 which are less in number than the conductors found in the sensor connector 5, 6. The reduction in the number of conductors is therefore accomplished by the support element 12 by electrically interconnecting 1305 the second plurality of conductors found in the cable half 5 of the sensor connector with the third plurality of conductors found in the cable 4 itself and correspondingly in the connector 3 that interfaces the probe 1 with the pulse oximeter instrument 2. The support element 12 can contain printed circuit wiring or a hard wired cross connect field in order to accomplish the circuit interconnection required to customize the interconnection of the elements contained within housing 7 to the specific electrical interconnection required by the pulse oximeter instrument 2. Yet another alternative interconnection methodology is the use of an interconnect arrangement contained within the connector 3 that interfaces the cable 4 to the pulse oximeter instrument 2 itself. Any of these arrangements perform the programmable function required to map the generic housing 7 with its sensor 16, 18, 20 and calibration 34 elements to the specific pulse oximeter instrument 2.

Therefore, the use of the inexpensive sensor connector 5, 6 with its anisotropically conducting elastomer provides a means for converting the expensive probes of the prior art into an inexpensive probe system 1 that comprises a reusable cable segment B and an inexpensive disposable universal housing segment A that can be used with all pulse oximeter instruments 2 due to the electrical programming capability of the cable segment B of the probe 1.

While a specific embodiment of this invention has been disclosed, it is expected that those skilled in the art can and will design alternate embodiments of this invention that fall within the scope of the appended claims.

I claim:

1. A sensor apparatus for measuring a physiological characteristic of a subject for a measurement system that has a connector for electrically connecting to a sensor to exchange signals therebetween, comprising:

housing means including:
    means for removably attaching said sensor to said subject,
    means, having a first plurality of electrical conductors, for generating electrical signals indicative of said measured physiological charactertistic of said subject,
    housing connector means connected to said first plurality of electrical conductors;

means for interconnecting said housing means to said measurement system connector, including:
    system connector means, releasably attachable to said measurement system a connector, for exchanging electrical signals therebetween,
    cable connector means, releasably attachable to said housing connector means, for exchanging electrical signals therebetween,
    means, connected to said system connector means and said cable connector means, for transmitting said generated electrical signals from said cable connector means to said system connector means, including means for programmably interconnecting said first plurality of electrical conductors to said measurement system connector.

2. The apparatus of claim 1 wherein said generating means includes:
    at least two light sources of different wavelengths for applying two beams of light to said subject,
    light detector means for producing said generated signals, indicative of a light intensity of said two beams of light,
    wherein said first plurality of electrical conductors are connected to said light sources, said light detector means and said housing connector means for exchanging said generated signals therebetween.

3. The apparatus of claim 2 wherein said removably attaching means includes:
    a flexible support structure for securing said light sources and said light detector means in optical contact with said subject.

4. The apparatus of claim 1 wherein said cable connector means includes:
    a second plurality of conductors,
    means for supporting said second plurality of conductors to interface with said first plurality of conductors in said housing connector means.

5. The apparatus of claim 4 wherein said measurement system connector contains a third plurality of conductors, which are lesser in number than said first plurality of conductors, and said first and second plurality of conductors are the same in number and interconnected on a one to one basis by said cable connector means, said programmably interconnecting means includes:
    means for joining at least two of said conductors in said first plurality of conductors to one of said conductors in said third plurality of conductors.

6. The apparatus of claim 1 wherein said measurement system connector contains a second plurality of conductors, which are lesser in number than said first plurality of conductors, said programmably interconnecting means includes:
    means for joining at least two of said conductors in said first plurality of conductors to one of said conductors in said second plurality of conductors.

7. The apparatus of claim 1 wherein said cable connector means includes:
    means for latching said interconnecting means to said housing connector means.

8. The apparatus of claim 1 further comprising:
    anisotropically conductive elastomer means to provide conductive paths from said first plurality of conductors to said transmitting means when said housing connector means and said cable connector means are physically joined together.

9. A sensor apparatus for measuring light absorption of blood perfused flesh of a subject for a pulse oximeter system that has a connector for electrically connecting to a sensor to exchange signals therebetween, comprising:

housing means including:
    at least two light sources of different wavelengths for applying two beams of light to said flesh,
    light detector means for producing said signals indicative of a light intensity of said two beams of light,
    means for removably attaching said light sources and said light detector means to said subject,
    a first plurality of electrical conductors connected to said light sources and said light detector means,
    housing connector means connected to said first plurality of electrical conductors;

means for connecting said housing means to said pulse oximeter system connector, including:
    system connector means, releasably attachable to said pulse oximeter system connector, for exchanging said signals therebetween
    cable connector means, releasably attachable to said housing connector means, for exchanging said signals therebetween,
    means, connected to said system connector means and said cable connector means for transmitting said signals from said cable connector means to said system connector means, including means for programmably interconnecting said first plurality of electrical conductors to said pulse oximeter system connector.

10. The apparatus of claim 9 wherein said removably attaching means includes:
    a flexible support structure for securing said light sources and said light detector means in optical contact with said subject.

11. The apparatus of claim 10 wherein said removably attaching means further includes:
    means for electrically insulating said first plurality of conductors from said flesh.

12. The apparatus of claim 9 wherein said cable connector means includes:
    a second plurality of conductors,
    means for supporting said second plurality of conductors to interface with said first plurality of conductors in said housing connector means.

13. The apparatus of claim 12 wherein said cable connector means further includes:
    anisotropically conductive elastomer means to provide conductive paths from said first plurality of conductors to said second plurality of conductors when said cable connector means and said housing connector means are physically joined together.

14. The apparatus of claim 12 wherein said pulse oximeter system connector contains a third plurality of conductors, which are lesser in number than said first plurality of conductors, and said first and second plurality of conducts are the same in number an interconnected on a one to one basis by said cable connector means, said programmably interconnecting means includes:
means for joining at least two of said conductors in said first plurality of conductors to one of said conductors in said third plurality of conductors.

15. The apparatus of claim 9 wherein said pulse oximeter system connector contains a second plurality of conducts, which are lesser in number than said first plurality of conductors, said programmably interconnecting means includes:
means for joining at least two of said conductors in said first plurality of conductors to one of said conductors in said second plurality of conductors.

16. The apparatus of claim 9 wherein said first plurality of conductors includes a lead frame, having a plurality of leads, that is deformable plastically.

17. The apparatus of claim 9 wherein said housing connector means comprises a first end of a flat flexible cable connector system.

18. The apparatus of claim 17 wherein said cable connector means comprises a second end of a flat flexible cable connector system for mating with said first end of said flat flexible cable connector system.

19. The apparatus of claim 18 wherein said cable connector means includes:
a second plurality of conductors,
means for supporting said second plurality of conductors to interface with said first plurality of conductors in said housing connector means.

20. The apparatus of claim 19 wherein said cable connector means further includes:
anisotropically conductive elastomer means to provide conductive paths from said first plurality of conductors to said second plurality of conductors when said housing connector means and said cable connector means are physically joined together.

21. The apparatus of claim 17 wherein said first and second ends of said flat flexible cable connector system are each shaped to be geometrically mating elements.

22. The apparatus of claim 17 wherein said first and second ends of said flat flexible connector system are configured as a pin and socket connector system.

23. The apparatus of claim 9 wherein said cable connector means includes:
means for latching to said housing connector means.

24. The apparatus of claim 23 wherein said latching means includes an opening of predetermined geometric shape to receive a tab element included in said housing connector means.

25. The apparatus of claim 24 wherein said latching means includes a user activated spring to release said tab element from said opening of said latching means.

26. A sensor apparatus for measuring a physiological characteristic of a subject for a measurement system that has a connector for electrically connecting to said sensor to exchange signals therebetween, comprising:
housing means including:
means for removably attaching said sensor to said subject,
means, having a first plurality of electrical conductors, for generating electrical signals indicative of said measured physiological characteristic,
housing connector means connected to said first plurality of electrical conductors;
means for connecting said probe means to said measurement system connector, including:
system connector means, releasably attachable to said measurement system connector, for exchanging said generated electrical signals therebetween,
cable connector means, releasably attachable to said housing connector means, for exchanging said generated electrical signals therebetween,
means connected to said system connector means and said cable connector means for transmitting said generated electrical signals from said cable connector means to said system connector means;
wherein said cable connector means includes anisotropically conductive elastomer means to provide conductive paths from said first plurality of conductors to said transmitting means when said housing connector means and said cable connector means are physically joined together.

27. The apparatus of claim 26 further comprising:
means for programmably interconnecting said first plurality of electrical conductors to said connector.

28. The apparatus of claim 26 wherein said generating means includes:
at least two light sources of different wavelengths for applying two beams of light to said subject,
light detector means for producing said signals indicative of a light intensity of said two beams of light received from said subject, and
wherein said first plurality of electrical conductors are connected to said light sources, said light detector means and said housing connector means for exchanging said signals therebetween.

29. The apparatus of claim 28 wherein said removably attaching means includes:
a flexible support structure for securing said light sources and said light detector means in optical contact with said subject.

30. The apparatus of claim 26 wherein said cable connector means includes:
a second plurality of conductors,
means for supporting said second plurality of conductors to interface with said first plurality of conductors in said housing connector means.

31. The apparatus of claim 30 wherein said measurement system connector contains a third plurality of conductors, which are lesser in number than said first plurality of conductors, and said first and second plurality of conductors are the same in number and interconnected on a one to one basis by said cable connector means, said programmably interconnecting means includes:
means for joining at least two of said conductors in said first plurality of conductors to one of said conductors in said third plurality of conductors.

32. The apparatus of claim 26 wherein said measurement system connector contains a second plurality of conductors, which are lesser in number than said first plurality of conductors, said programmably interconnecting means includes:
means for joining at least two of said conductors in said first plurality of conductors to one of said conductors in said second plurality of conductors.

33. The apparatus of claim 26 wherein said cable connector means includes:
means for latching said cable connector means to said housing connector means.

34. The apparatus of claim 33 wherein said first plurality of conductors include a lead frame, having a plurality of leads, that is deformable plastically.

35. The apparatus of claim 33 wherein said housing connector means comprises a first end of a flat flexible cable connector system.

36. The apparatus of claim 35 wherein said first and second ends of said flat flexible cable connector system are each shaped to be geometrically mating elements.

37. The apparatus of claim 35 wherein said first and second ends of said flat flexible connector system are configured as a pin and socket connector system.

38. The apparatus of claim 35 wherein said cable connector means comprises a second end of a flat flexible cable connector system for mating with said first end of said flat flexible cable connector system.

39. The apparatus of claim 38 wherein said cable connector means includes:
 a second plurality of conductors,
 means for supporting said second plurality of conductors to interface with said first plurality of conductors in said housing connector means.

40. The apparatus of claim 33 wherein said cable connector means includes:
 means for latching to said housing connector means.

41. The apparatus of claim 40 wherein said latching means includes an opening of predetermined geometric shape to receive a tab element included in said housing connector means.

42. The apparatus of claim 41 wherein said latching means includes a user activated spring to release said tab element from said opening of said latching means.

43. A sensor apparatus for measuring light absorption of blood perfused flesh of a subject for a pulse oximeter system that has a connector for electrically connecting to said sensor to exchange signals therebetween, comprising:
 probe means including:
  at least two light sources of different wavelengths for applying two beams of light to said flesh,
  light detector means for producing said signals indicative of a light intensity of said two beams of light received from said subject,
  means for removably attaching said light sources and said light detector means to said subject,
 a first plurality of electrical conductors connected to said light sources and said light detector means,
 housing connector means connected to said first plurality of electrical conductors;
 means for connecting said probe means to said pulse oximeter system connector, including:
  system connector means, releasably attachable to said pulse oximeter system connector, for exchanging said generated electrical signals therebetween,
  cable connector means, releasably attachable to said housing connector means, for exchanging said generated electrical signals therebetween,
  means, connected to said system connector means and said cable connector means, for transmitting said generated electrical signals from said cable connector means to said system connector means,
 wherein said housing means includes anisotropically conductive elastomer means to provide conductive paths from said first plurality of conductors to said transmitting means when said housing connector means and said cable connector means are physically joined together.

44. The apparatus of claim 43 further comprising:
 means for programmably interconnecting said first plurality of electrical conductors to said pulse oximeter system connector.

45. The apparatus of claim 43 wherein said removably attaching means includes:
 a flexible support structure for securing said light sources and said light detector means in optical contact with said subject.

46. The apparatus of claim 45 wherein said removably attaching means further includes:
 means for electrically insulating said first plurality of conductors from said flesh.

47. The apparatus of claim 43 wherein said cable connector means includes:
 a second plurality of conductors,
 means for supporting said second plurality of conductors to interface with said first plurality of conductors in said housing connector means.

48. The apparatus of claim 46 wherein said pulse oximeter system connector contains a third plurality of conductors, which are lesser in number than said first plurality of conductors, and said first and second plurality of conductors are the same in number and interconnected on a one to one basis by said cable connector means, said programmably interconnecting mans includes:
 means for joining at least two of said conductors in said first plurality of conductors to one of said conductors in said third plurality of conductors.

49. The apparatus of claim 43 wherein said pulse oximeter system connector contains a second plurality of conductors, which are lesser in number than said first plurality of conductors, said programmably interconnecting means includes:
 means for joining at least two of said conductors in said first plurality of conductors to one of said conductors in said second plurality of conductors.

* * * * *